United States Patent
Tonigold et al.

(10) Patent No.: US 10,293,333 B2
(45) Date of Patent: May 21, 2019

(54) CATALYST CONTAINING PHOSPHORUS FOR CONVERTING OXYGENATES INTO OLEFINS

(71) Applicant: Clariant Produkte (Deutschland) GmbH, Frankfurt am Main (DE)

(72) Inventors: Markus Tonigold, Holzkirchen (DE); Manfred Frauenrath, Grosskarolinenfeld (DE); Goetz Burgfels, Bad Aibling (DE)

(73) Assignee: CLARIANT PRODUKTE (DEUTSCHLAND) GMBH (DE)

( * ) Notice: Subject to any disclaimer, the term of this patent is extended or adjusted under 35 U.S.C. 154(b) by 10 days.

(21) Appl. No.: 15/105,877

(22) PCT Filed: Dec. 8, 2014

(86) PCT No.: PCT/EP2014/076938
§ 371 (c)(1),
(2) Date: Jun. 17, 2016

(87) PCT Pub. No.: WO2015/091078
PCT Pub. Date: Jun. 25, 2015

(65) Prior Publication Data
US 2016/0318007 A1    Nov. 3, 2016

(30) Foreign Application Priority Data
Dec. 20, 2013 (DE) .......... 10 2013 021 950

(51) Int. Cl.
| | | |
|---|---|---|
| B01J 29/40 | (2006.01) | |
| B01J 37/28 | (2006.01) | |
| B01J 37/00 | (2006.01) | |
| B01J 37/08 | (2006.01) | |
| C07C 1/20 | (2006.01) | |
| B01J 35/00 | (2006.01) | |
| B01J 35/02 | (2006.01) | |
| C01B 39/40 | (2006.01) | |
| B01J 29/70 | (2006.01) | |
| C01B 39/02 | (2006.01) | |
| B01J 35/10 | (2006.01) | |

(52) U.S. Cl.
CPC .......... *B01J 29/40* (2013.01); *B01J 29/7023* (2013.01); *B01J 29/7034* (2013.01); *B01J 29/7042* (2013.01); *B01J 29/7046* (2013.01); *B01J 35/006* (2013.01); *B01J 35/0013* (2013.01); *B01J 35/023* (2013.01); *B01J 37/0018* (2013.01); *B01J 37/08* (2013.01); *B01J 37/28* (2013.01); *C01B 39/026* (2013.01); *C01B 39/40* (2013.01); *C07C 1/20* (2013.01); *B01J 29/70* (2013.01); *B01J 35/1019* (2013.01); *B01J 35/1038* (2013.01); *B01J 37/0063* (2013.01); *B01J 2229/186* (2013.01); *B01J 2229/20* (2013.01); *B01J 2229/36* (2013.01); *B01J 2229/37* (2013.01); *B01J 2229/42* (2013.01); *C07C 2521/02* (2013.01); *C07C 2521/04* (2013.01); *C07C 2527/14* (2013.01); *C07C 2529/40* (2013.01)

(58) Field of Classification Search
CPC ....................................................... B01J 29/40
See application file for complete search history.

(56) References Cited

U.S. PATENT DOCUMENTS

| | | | |
|---|---|---|---|
| 4,356,338 A | 10/1982 | Young | |
| 6,040,257 A * | 3/2000 | Drake | B01J 29/40 |
| | | | 502/208 |
| 7,229,941 B2 | 6/2007 | Burgfels et al. | |
| 8,349,758 B2 | 1/2013 | Gabriel et al. | |
| 2011/0152479 A1* | 6/2011 | Nesterenko | B01J 21/08 |
| | | | 526/75 |
| 2011/0178259 A1 | 7/2011 | Nesterenko et al. | |
| 2013/0156688 A1 | 6/2013 | Burgfels et al. | |
| 2013/0197291 A1 | 8/2013 | Nesterenko et al. | |
| 2014/0058180 A1 | 2/2014 | Klingelhofer et al. | |
| 2015/0231614 A1* | 8/2015 | Jana | B01J 29/7007 |
| | | | 585/510 |
| 2017/0267523 A1 | 9/2017 | Nakamura et al. | |

FOREIGN PATENT DOCUMENTS

| | | |
|---|---|---|
| DE | 10 2011 013 909 | 9/2012 |
| EP | 0 123 449 | 10/1984 |
| EP | 0 448 000 | 9/1991 |
| EP | 1 424 128 | 2/2004 |
| EP | 2 348 004 | 7/2011 |
| JP | S59-199639 | 11/1984 |
| WO | WO 03/020667 * | 3/2003 |
| WO | WO 2007/076088 | 5/2007 |

(Continued)

OTHER PUBLICATIONS

Synthesis and Structure of Zeolite ZSM-5: A Raman Spectroscopic Study Prabir Dutta et al. J. Phys. Chem. vol. 91, pp. 4329-4333, (Year: 1987).*
PCT international Search Report for PCT/EP2014/076938, dated Mar. 4, 2015.
EP 0 448 000, Machine English Translation, Sep. 25, 1991.

*Primary Examiner* — Douglas B Call

(57) ABSTRACT

The present invention relates to a novel process for preparing a phosphorus-containing catalyst, in which a steam treatment of the catalyst is effected, and to the catalyst obtainable thereby, and to the use thereof in a process for preparing olefins from oxygenates. The steam treatment of the catalyst typically precedes modification of the catalyst with a phosphorus compound.

22 Claims, 7 Drawing Sheets

(56) References Cited

FOREIGN PATENT DOCUMENTS

| WO | WO 2009/156434 | | 12/2009 |
|----|----------------|---|---------|
| WO | WO 2011/044037 | | 4/2011 |
| WO | WO 2012/123556 | | 9/2012 |
| WO | WO 2012/123557 | | 9/2012 |
| WO | WO 2012/123558 | | 9/2012 |
| WO | WO 2013/017499 | | 7/2013 |
| WO | WO 2014/027311 | * | 2/2014 |

* cited by examiner

CATALYST CONTAINING PHOSPHORUS FOR CONVERTING OXYGENATES INTO OLEFINS

The present invention relates to a process for preparing phosphorus-containing zeolite-based catalysts, to the catalysts prepared by this process and to the use thereof in a process for converting oxygenates to olefins. The invention relates particularly to the conversion of methanol or dimethyl ether to olefins (CMO process). More particularly, the invention also relates to the conversion of methanol to propylene.

BACKGROUND OF THE INVENTION

The catalyzed conversion of oxygenates to olefins, especially of methanol to propylene, is an attractive way of creating value because of the upgrading of the starting materials. Zeolite-based catalysts for conversion of oxygenates to olefins are described, for example, in EP 0 448 000 A1 and EP 1 424 128 A1.

A general problem in the case of use of zeolite-based catalysts in the conversion of oxygenates to olefins is that the catalysts tend to lose catalytic activity over the course of the process. This is brought about firstly by the increasing carbonization of the surfaces and pores. This arises because the by-products that form during the conversion of oxygenates to olefins can condense to form longer-chain or cyclic species and be deposited on the catalyst, resulting in masking of the catalytically active sites. Therefore, after a particular service life, what is called a regeneration is necessary, in which the carbonaceous deposits are removed from the catalyst under mild conditions. Secondly, the reaction conditions also bring about progressive dealumination of the zeolitic material. This is caused by the steam which arises, for example, in the case of use of water-containing feeds and/or in the conversion reaction of the oxygenates to olefins. The result of the dealumination is that the number of catalytically active sites gradually decreases, the catalyst is irreversibly deactivated and the conversion rate of the oxygenate used decreases.

To influence the activity, stability or selectivity, the prior art describes the modification of zeolite-based catalysts with phosphorus at different times in the production process, and the use of washing or steam treatments.

WO 2012/123558 and WO 2012/123556 describe the preparation of a phosphorus-modified zeolite-based catalyst by applying a phosphorus compound to an extruded and calcined zeolite. WO 2012/123557 describes the preparation of a phosphorus-containing zeolite-based catalyst by extrusion of a phosphorus-modified zeolite followed by a final calcination. These preparation processes do not include a steam treatment; by contrast, the catalysts obtained have to be subjected to a steam treatment prior to use in an MTO process.

U.S. Pat. No. 4,356,338 describes a process for reducing the level of carbon deposits and prolonging the service life of a zeolitic catalyst, by subjecting it to a steam treatment and/or a treatment with phosphorus compounds. This catalyst is notable for a lower tendency to carbonization in use as catalyst for the aromatization of 1-heptene, and it is simultaneously possible to observe a lowering of the output yields. The catalyst has phosphorus contents between 2% and 15% by weight.

WO 2011/044037 describes a zeolite-based catalyst which is prepared by treating a zeolite with a phosphorus compound. The phosphorus-treated zeolite is admixed with a binder, extruded, calcined and contacted with liquid water, removing a portion of the phosphorus from the phosphorus-treated zeolite. The catalyst described in WO 2011/044037, after prior steam treatment, is used in processes for alkylating aromatics.

EP 2 348 004 A1 describes a process for preparing a phosphorus-modified zeolite-based catalyst and the use of the catalyst in an MTO process. In this process, steam treatment reduces the aluminum content of a ZSM-5 zeolite. The catalyst is then prepared by applying phosphorus to the zeolite and then mixing the phosphorus-modified zeolite with one or more binders, alkaline earth metal salts, rare earth metal salts, clays and shaping additives.

WO 2009/156434 describes a process for preparing lower olefins, by providing an XTO reaction zone, an OC reaction zone and a catalyst regeneration zone, using a phosphorus-modified zeolite-based catalyst. Prior to the application of phosphorus with a solution, a zeolite is subjected to a steam treatment at a temperature of 400° C. to 870° C. for 0.01 to 200 h and optionally mixed with a binder, and a portion of the aluminum is removed by leaching with an aqueous acid solution.

WO 2007/076088 relates to a process for preparing a phosphorus-modified zeolite-based catalyst and to the use of the catalyst in a toluene methylation process. The zeolite is modified with phosphorus and then bound with an inorganic oxide binder which has been treated with mineral acid. Prior to the use in the toluene methylation process, the catalyst is treated with steam at a temperature of 300° C. or less.

The crucial disadvantage of known non-phosphorus-modified catalysts for the conversion of oxygenates such as methanol or dimethyl ether to lower olefins and specifically the conversion of methanol to propylene is still deactivation as a result of carbonization within one cycle and the dealumination of the catalysts because of the presence of water during the catalytic conversion over several cycles. It is found in the case of use of phosphorus-modified catalysts that the modification does bring about an increase in the methanol conversion rate, but the existing preparation methods, on the other hand, lead to a disadvantageous decrease in propylene yield or propylene selectivity (to a greater or lesser degree according to the modification process used and phosphorus content). However, a lowered propylene selectivity reduces the economic viability of the process.

Even with the known processes for converting methanol to propylene using non-phosphorus-modified catalysts, propylene selectivities are achieved that can still be optimized. In general, in the conversion of oxygenates such as methanol or dimethyl ether to lower olefins, especially of methanol to propylene, the propylene selectivity increases with rising temperature. On the other hand, however, deactivation as a result of carbonization and dealumination also increases drastically in processes for converting oxygenates to olefins with rising temperature. An increase in selectivity by increasing the temperature in the reactor in the conversion of oxygenates such as methanol or dimethyl ether to olefins is thus desirable, provided that the known disadvantages for the performance of the catalyst can be overcome.

It is known from the prior art that phosphorus modifications of zeolite-based catalysts can prolong the lifetime thereof. The term "lifetime" in this connection is understood to mean the duration of the catalyzed conversion to hydrocarbons until the same conversion of, for example, not less than 95% is attained. Experiments on modified catalysts prepared according to the prior art show that phosphorus modifications of formed extrudates under relevant process conditions (for example addition of water, for instance in a water:methanol weight ratio of 2:1) can have an adverse effect on olefin selectivity, particularly on the selective release of propylene. The overall cumulated propylene yield obtained over one cycle cannot be increased to a maximum degree by an increase in temperature, since either the drastic shortening of lifetime in the case of phosphorus-free catalysts or the decrease in the propylene selectivity in the case of phosphorus-modified catalysts has an adverse effect. It is thus not possible with the catalysts from the prior art to achieve a maximum increase in the olefin yield for the process for conversion of oxygenates such as methanol or dimethyl ether to olefins by increasing the temperature.

OBJECT OF THE INVENTION

It is an object of the present invention to provide a preparation process for a catalyst having an elevated methanol conversion rate without reduction in the selectivity for propylene. More particularly, the catalyst is to enable an elevated olefin yield with at least the same lifetime by increasing the temperature in the process for converting oxygenates such as methanol or dimethyl ether to lower olefins, i.e. have an elevated resistance to carbonization and dealumination.

It is a further object of the invention to provide a simplified preparation process for a catalyst, in which further process steps such as a subsequent washing after application of a phosphorus compound, a repeated modification with a phosphorus compound in a later process step or a further treatment with an acid to reduce the aluminum content after the steam treatment are dispensed with.

It is therefore also a further object of the present invention to provide a process which allows the preparation of a catalyst which can be used directly by the process user without time-consuming and costly steam treatment prior to the catalytic conversion reaction.

These objects are achieved by the process of the invention and the catalyst obtainable thereby.

SUMMARY OF THE INVENTION

The invention relates to a process for preparing a phosphorus-containing catalyst, comprising the following steps:
  (a) extruding a mixture comprising a zeolite and a binder,
  (b) calcining the extrudate obtained in step (a),
  (c) treating the calcined extrudate obtained in step (b) with steam,
  (d) applying a phosphorus compound to the steam-treated extrudate from step (c), and
  (e) calcining the phosphorus-modified extrudate from step (d), where the proportion by weight of phosphorus in the catalyst obtained after step (e) is 0.8% to 2.5% by weight, preferably from 1.0% to 1.8% by weight, and even more preferably about 1.4% by weight, based on the total weight of the catalyst.

It has been found that, surprisingly, the catalysts obtained by the process of the invention, in the preparation of lower olefins from oxygenates, especially from methanol or dimethyl ether, have an improved conversion rate of the oxygenate and an increased lifetime with the same selectivity, especially for propylene. Especially at elevated process temperature, the catalyst, by virtue of its elevated resistance to carbonization and dealumination, enables an increase in the propylene yield with at least the same lifetime compared to a non-phosphorus-modified catalyst.

The invention therefore further relates to a catalyst obtainable by this process, to the use of the catalyst for conversion of oxygenates such as methanol or dimethyl ether to olefins, especially of methanol to propylene, and to a process for preparing lower olefins from oxygenates such as methanol or dimethyl ether, wherein a reactant gas, preferably comprising methanol, dimethyl ether or a mixture thereof, is passed over the catalyst. The catalyst of the invention is typically used in an isothermal or adiabatic fixed bed reactor.

DETAILED DESCRIPTION OF THE INVENTION

Figure 1:
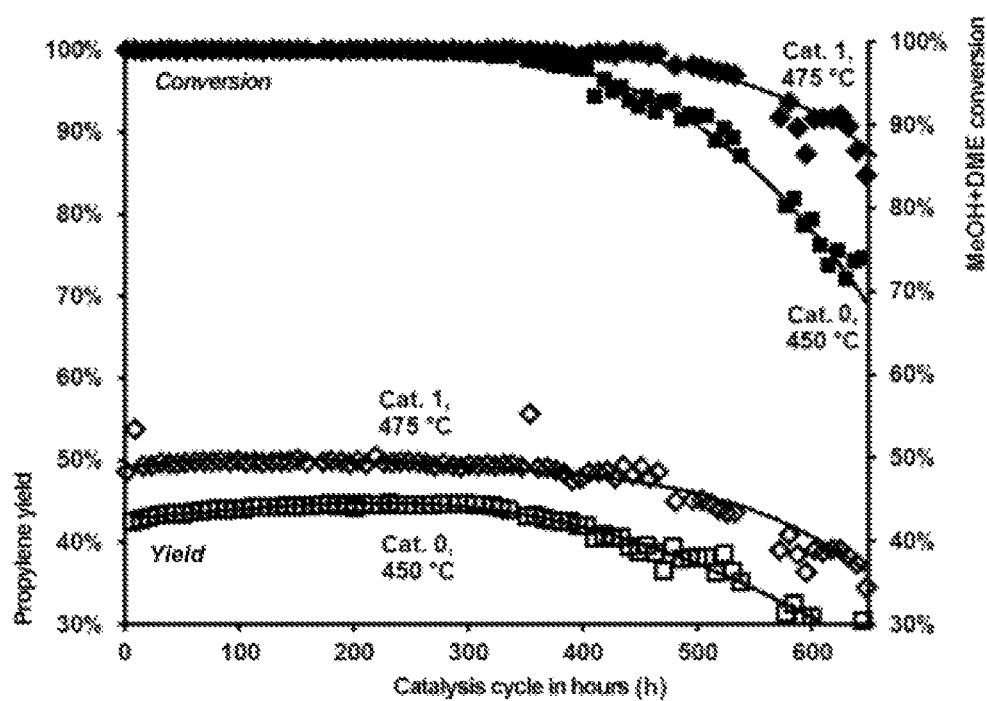
FIG. 1 shows the conversion of methanol to propylene over reference catalyst 0 at 450° C. and over inventive catalyst 1 at 475° C. Cat. 0: methanol conversion ■, propylene yield □; Cat. 1: methanol conversion ♦, propylene yield ◊. Steam treatment for 48 h in each case.

The invention relates to a process for preparing a phosphorus-containing catalyst, comprising the following steps:
  (a) extruding a mixture comprising a zeolite and a binder,
  (b) calcining the extrudate obtained from step (a),
  (c) treating the calcined extrudate obtained from step (b) with steam,
  (d) applying a phosphorus compound to the steam-treated extrudate from step (c), and
  (e) calcining the phosphorus-modified extrudate from step (d), where the proportion by weight of phosphorus in the catalyst obtained after step (e) is 0.8% to 2.5% by weight, preferably from 1.0% to 1.8% by weight, and even more preferably about 1.4% by weight, based on the total weight of the catalyst.

In a preferred embodiment, the zeolite used in step (a) has a phosphorus content of 0% by weight to 0.01% by weight, preferably of 0% by weight to 0.001% by weight to. It is particularly preferable that the zeolite used in step (a), within the scope of the detection limit, is phosphate-free.

It has been found that, surprisingly, in contrast to the teaching from the prior art, the washing of the catalyst after phosphorus modification does not bring about an improvement in the propylene selectivity or the lifetime. In the case of the catalyst of the invention, the washing after modification instead resulted in an adverse effect on the lifetime.

Without wishing to be bound to the theory which follows, the unchanged propylene selectivity of the inventive catalyst is explained by the presumed influence of the preparation steps on the acidity of the catalyst obtained. The acidity of a (non-phosphorus-modified) zeolite can be lowered by steam treatment. As described in Lago et al. in New Developments in Zeolite Science and Technology, editors: Y. Murakami, A. Iijima, and J. W. Ward, Elsevier, Tokyo, 1986, pages 677 ff., there is an increase here in the activity of the remaining acidic sites in the conversion of oxygenates to olefins. The zeolite obtained as a result is notable both for improved hydrothermal stability and for elevated propylene selectivity compared to a non-steam-treated zeolite.

It is known from the prior art that a phosphorus modification can increase the hydrothermal stability of a zeolite. If the phosphorus modification on the zeolite precedes the steam treatment, the acidic sites should be stabilized via the interaction with the phosphorus compounds present, such that the above-described effect of steam treatment loses effectiveness compared to non-phosphorus-containing zeolite. If the steam treatment, in accordance with the invention, is conducted prior to the modification with a phosphorus compound, the steam treatment is effective, and the subsequent phosphorus modification protects the sites modified beforehand via steam treatment and makes a contribution to a further increase in stability without losses of selectivity (as a result of the otherwise lower efficiency of the steam treatment).

Furthermore, probably depending on the treatment of the catalyst, other phosphorus compounds or a different distribution between the phosphorus compounds (for example isolated monophosphate, oligophosphates) can arise, with resulting altered interaction between the phosphorus compounds and the acidic sites of the zeolite, but also between the phosphorus compounds and the acidic sites of the binder.

In a preferred embodiment of the process of the invention (comprising steps (a) to (e)), treatment with steam is effected solely in step (c). This means that, between the extrusion of the mixture comprising zeolite and binder in step (a) and the calcination of the extrudate (obtained in step (a)) in step (b), there is no treatment with steam. Likewise preferably, after the application of a phosphorus compound in step (d), no treatment with steam is conducted. It is particularly preferable that no water treatment takes place either between steps (a) and (b) or after step (d).

In a preferred embodiment of the process of the invention (comprising steps (a) to (e)), application of a phosphorus compound is effected solely in step (d). This means that, more particularly, there is no application of a phosphorus compound either prior to the treatment of the extrudate with steam in step (c) or after the calcination of the phosphorus-modified extrudate in step (e).

The process of the invention for preparing the catalyst gives rise to the following advantages over the prior art: an increased lifetime of the catalyst without reduction in the propylene selectivity and a greatly increased lifetime at elevated temperature in the process for conversion of oxygenates such as methanol or dimethyl ether to lower olefins. No further time-consuming and costly steam treatment by the process operator is necessary. Compared to other post-synthetic modifications according to the prior art, further process steps that are necessary therein such as subsequent washing after application of the phosphorus compound, repeated modification with a phosphorus compound in a later process step or a further treatment with an acid to reduce the aluminum content after the steam treatment are dispensed with.

Oxygenates are understood in the context of the present invention to mean oxygen compounds, especially organic oxygen compounds such as alcohols and ethers. The oxygen compounds converted in accordance with the invention are preferably methanol (Conversion of Methanol to Olefins, CMO) or dimethyl ether. The present invention preferably relates to a process for producing lower olefins from oxygen compounds, the term "lower olefins" preferably being understood to mean olefins having a chain length of $C_2$ to $C_6$.

The zeolite used in step (a) is typically a crystalline aluminosilicate zeolite. The zeolite may have a structure as described in the "Atlas of Zeolite Framework Types" (Ch. Baerlocher, W. M. Meier, D. H. Olson, Elsevier, Fifth Revised Edition, 2001), the disclosure of which in this respect is hereby incorporated into the description. Suitable zeolite materials are, for example, zeolites with TON structure (e.g. ZSM-22, ISI-1, KZ-2), MTT structure (e.g. ZSM-23, KZ-1), MFI structure (e.g. ZSM-5), MEL structure (e.g. ZSM-11), MTW structure (e.g. ZSM-12), zeolites with EUO structure or else ZSM-21, ZSM-35, ZSM-38, ZSM-4, ZSM-18 or ZSM-57. More particularly, the zeolite has a TON structure, MTT structure, MFI structure, MEL structure, MTW structure or EUO structure. It is also possible to use mixtures of zeolites of different structure.

Preferably, the zeolite used in step (a) is a zeolite of the pentasil type; more preferably, the zeolite has an MFI structure, especially of the ZSM-5 type. It is further preferable that the zeolites are present in the H form, i.e. the protonated form.

The process for preparing crystalline aluminosilicate zeolites particularly suitable for conversion of oxygenates such as methanol or dimethyl ether to lower olefins is described in general terms in EP 1 424 128 B1, the disclosure of which in this respect is hereby explicitly incorporated into the present description.

The zeolite used in step (a) preferably consists of primary aluminosilicate crystallites having a mean diameter in the range from 0.010 μm to 0.100 μm, more preferably in the range from 0.010 μm to 0.060 μm, and most preferably in the range from 0.015 μm to 0.050 μm. It has been found that, in the performance of the process of the invention, there is typically no change or only a slight change in the primary crystallite size of the zeolite used. Preferably, therefore, the catalyst obtainable by the process of the invention also contains a zeolite consisting of aluminosilicate primary crystallites having a mean diameter in the range from 0.010 μm to 0.100 μm, more preferably in the range from 0.010 μm to 0.060 μm, and most preferably in the range from 0.015 μm to 0.050 μm.

The mean diameter of the primary crystallites is defined as the arithmetic mean of the mean diameter of a multitude of crystallites (for example from 10 to 100, preferably 10 to 20, for example 14 or 15), the mean diameter of the individual crystallites being defined as the arithmetic mean between the greatest and smallest diameters of a single crystallite, the greatest and smallest diameter of a crystallite being determined on the basis of scanning electron microscopy analyses at a magnification of 80 000. This definition is of significance in the case of crystallites having an irregular crystal habit, for example in the case of rod-shaped crystallites. In the case of spherical or nearly spherical crystallites, the greatest and smallest diameters coincide.

The zeolite used in step (a) preferably has an Si/Al atomic ratio in the range from 50 to 250, preferably in the range from 50 to 150, especially in the range from 75 to 140, even more preferably in the range from 85 to 125.

The binder used in step (a) in the process of the invention typically comprises inorganic oxides, especially aluminum oxide, magnesium oxide, titanium oxide, zinc oxide, niobium oxide, zirconium oxide, silicon oxide, and/or hydrates thereof, and mixtures thereof, for example mixtures of the aforementioned oxides (except for aluminum oxide) with aluminum oxide. For example, it is also possible to use amorphous aluminosilicates and non-oxidic binders, for example aluminum phosphates. Preferably, the binder used in step (a) is an aluminum oxide, which can also be used in the form of aluminum oxide hydrate or of modified aluminum oxide. Modified aluminum oxide is, for example, phosphorus-modified aluminum oxide. Particular preference is given to the use of finely divided aluminum oxide which is obtained, for example, by hydrolysis of aluminum trialkyls or aluminum alkoxides, or is used in the form of peptizable aluminum oxide hydrate. Very particular preference is given to using peptizable aluminum oxide hydrate as binder. Preferably, at least 95% of the particles of the peptizable aluminum oxide hydrate have a mean diameter of 100 μm, measured by laser diffraction. The determination was effected using a MALVERN MasterSizer 2000 with 2000 S dispersing unit; the measurement was effected in accordance with ISO 13320.

It is preferable to use the binder in step (a) in an amount in the range from 5% to 60% by weight, more preferably in the range from 8% to 40% by weight, especially preferably in the range from 10% to 35% by weight, based on the total weight of zeolite used and binder.

It is additionally preferable that the mixture in step (a) comprises an inorganic or organic acid, especially sulfuric acid, nitric acid, acetic acid, formic acid, oxalic acid or citric acid, preferably nitric acid, acetic acid or citric acid, more preferably citric acid and/or nitric acid. It is additionally preferable that the mixture in step (a) comprises the acid, if present, in aqueous solution.

In addition, the mixture in step (a) may also comprise additives (for example oils, paraffin wax, methyl cellulose or polyethylene oxide).

The mixture extruded in step (a), comprising a zeolite, a binder and, for example, an inorganic or organic acid and/or additives is typically obtained by mixing the components with a commercially available mixer, for example a mixer having moving mixing tools and a fixed chamber or a mixer having moving mixing tools and a moving chamber.

The extrusion of the binder-zeolite mixture (the term "binder-zeolite mixture" as used here also including mixtures which may comprise other constituents such as an inorganic or organic acid and/or additives) in step (a) is effected by using a conventional extruder, for example a single-shaft extruder or twin-shaft extruder. More particularly, the shaping (i.e. extrusion) in step (a) may proceed from a plasticizable mass of the binder-zeolite mixture, which, on completion of shaping, is subjected to a calcination in step (b), in order to obtain the desired stability.

In the process of the invention, the calcination in step (b) or step (e) is typically conducted for 10 min to 15 h, preferably for 1 h to 10 h. The calcination temperature is typically within a range from 350° C. to 700° C., preferably within a range from 400° C. to 700° C., especially within a range from 500° C. to 600° C., especially preferably about 550° C. It is particularly preferable that the calcination in step (b) is conducted for 1 h to 10 h, especially for 5 h, at a temperature in the range from 400° C. to 700° C., especially within a range from 500° C. to 600° C., and more preferably for about 5 h at about 550° C. It is further preferable that the calcination in step (e) is conducted for 1 h to 10 h, especially for 5 h, at a temperature in the range from 400° C. to 700° C., especially in the range from 500° C. to 600° C., and more preferably for about 5 h at a temperature of about 550° C.

In a particularly preferred embodiment, the calcination in both steps (b) and (e) is conducted for 1 h to 10 h, especially for 5 h, at a temperature in the range from 400° C. to 700° C., especially in the range from 500° C. to 600° C., and more preferably for about 5 h at about 550° C.

The extrudate obtained from step (a) or from step (d) is preferably dried before it is subjected to the calcination step (b) or the calcination step (e). The drying is usually conducted for 5 min to 24 h at a temperature in the range from 50° C. to 150° C., preferably for 1 to 10 h at a temperature in the range from 80° C. to 150° C. and more preferably for about 5 h at about 120° C.

In a preferred embodiment, the invention relates to a process for preparing a phosphorus-containing catalyst, comprising the following steps:
(a) extruding a mixture comprising a zeolite and a binder,
(b) drying and calcining the extrudate obtained from step (a),
(c) treating the calcined extrudate obtained from step (b) with steam,
(d) applying a phosphorus compound to the steam-treated extrudate from step (c), and
(e) drying and calcining the phosphorus-modified extrudate from step (d), where the proportion by weight of phosphorus in the catalyst obtained after step (e) is 0.8% to 2.5% by weight, preferably from 1.0% to 1.8% by weight, and even more preferably about 1.4% by weight, based on the total weight of the catalyst.

In an even more preferred embodiment, the invention relates to a process for preparing a phosphorus-containing catalyst, comprising the following steps:
(a) extruding a mixture comprising a zeolite and a binder,
(b) drying and calcining the extrudate obtained from step (a),
(c) treating the calcined extrudate obtained from step (b) with steam,
(d) applying a phosphorus compound to the steam-treated extrudate from step (c), and
(e) drying and calcining the phosphorus-modified extrudate from step (d), where the proportion by weight of phosphorus in the catalyst obtained after step (e) is 0.8% to 2.5% by weight, preferably from 1.0% to 1.8% by weight, and even more preferably about 1.4% by weight, based on the total weight of the catalyst, and wherein the drying both in step (b) and in step (e) is conducted at a temperature in the range from 80° C. to 150° C. for 1 to 10 h, preferably 6 to 8 h, and the calcination both in step (b) and in step (e) is conducted at a temperature in the range from 500° C. to 600° C. for 6 to 8 h.

Typically, the process of the invention avoids contacting of the catalyst with water after the calcination step (e); more particularly, after step (e), no further steam treatment is conducted prior to use in a process for converting oxygenates such as methanol or dimethyl ether to olefins.

The treatment with steam in step (c) is typically conducted at a partial steam pressure in the range from 0.1 to 1 bar, a temperature in the range from 400° C. to 850° C., a WHSV (weight hourly space velocity) in the range from 0.01 to 10 h$^{-1}$ and for 0.5 to 100 h, preferably at a partial steam pressure of about 1 bar, a temperature of 400° C. to 650° C. (especially from 480° C. to 550° C.), a WHSV of about 1 h$^{-1}$ and a duration of about 48 h.

The phosphorus compound can be applied in solid form or in solution in step (d). It is preferable that the phosphorus compound is used in solution.

In the process of the invention, the phosphorus compound is preferably selected from inorganic phosphorus acids, organic phosphorus acids, alkali metal salts, alkaline earth metal salts and/or ammonium salts of inorganic phosphorus acids or organic phosphorus acids, phosphorus(V) halides, phosphorus(III) halides, phosphorus oxide halides, phosphorus(V) oxide, phosphorus(III) oxide and mixtures thereof.

In the process of the invention, it is further preferable that the phosphorus compound is independently selected from $PY_5$, $PY_3$, $POY_3$, $M_xE_{z/2}H_{3-(x+z)}PO_4$, $M_xE_{z/2}H_{3-(x+z)}PO_3$, $P_2O_5$ and $P_4O_6$, in which Y is F, Cl, Br or I, preferably Cl, x=0, 1, 2 or 3, z=0, 1, 2 or 3, where x+z≤3, M is independently alkali metal and/or ammonium, and E is alkaline earth metal.

In an even more preferred embodiment, the phosphorus compound used in the process of the invention is $H_3PO_4$, $(NH_4)H_2PO_4$, $(NH_4)_2HPO_4$ and/or $(NH_4)_3PO_4$. In the process of the invention, it is preferable that the phosphorus compound is $H_3PO_4$ or $(NH_4)H_2PO_4$, and especially preferably that the phosphorus compound is $H_3PO_4$.

The application of the phosphorus compound from aqueous solution (impregnation solution) is effected, for example, by a "wet impregnation" method or an "incipient wetness" method. In the "wet impregnation" method, the extrudate is typically first suspended in the phosphorus-containing solution and the suspension, for improved interaction of the phosphorus compound with the extrudate, is optionally heated to a temperature in the range from 45° C. to 95° C. Subsequently, the water in the impregnation solution is removed in the gaseous state, especially removed completely by distillation at elevated temperature in the range from 75° C. to 115° C. and/or a pressure of 0.1 MPa to 0.1 MPa. The distillative removal of the water in the impregnation solution can be conducted, for example, using a rotary evaporator.

In the "incipient wetness" method (also referred to as the pore filling method), the extrudate is contacted with the phosphorus-containing solution, the volume of the phosphorus-containing solution corresponding to the pore volume of the extrudate. This means that the volume of the phosphorus-containing solution is matched to the adsorption volume of the extrudate such that no excess solution is present any longer on completion of impregnation. The volume required for the purpose can be determined by adding an accurately weighed amount of the extrudate material to be impregnated into a solution consisting of distilled water, the extrudates being fully covered by the aqueous solution. After the solution has been left to stand for a sufficient period, typically h, the solution is decanted off and the still-moist extrudates are weighed again. The increase in weight, with knowledge of the density of the solution, can be used to calculate the volume absorbed, which corresponds to the volume of the phosphorus-containing solution in the case of the "incipient wetness" loading with the phosphorus-containing solution as well. The water in the phosphorus-containing solution can then be partly or fully removed in the subsequent drying and calcination. Such a course of action enables exact and reproducible application of the phosphorus compound. Alternative methods to the "incipient wetness" method are coating methods, for example using an Aircoater™ or Huttlin coater (from Innojet Herbert Huttlin, Germany).

If the phosphorus compound is applied to the extrudate in the form of a solution in step (d), the product obtained is typically dried as described above before it is subjected to the calcination step (e). The drying is usually conducted within the range from 5 min to 24 h at a temperature in the range from 50° C. to 150° C., preferably at a temperature in the range from 80° C. to 150° C., and preferably for about 5 h at about 120° C.

The phosphorus content is preferably controlled by the method of application, more preferably by application by incipient wetness, as a result of which the entire amount of phosphorus present in the solution is applied to the extrudates.

The catalyst obtainable by the process of the invention preferably has a phosphorus content of 0.8% to 2.5% by weight, more preferably of 1.0% to 1.8% by weight, and most preferably of about 1.4% by weight, based on the total weight of the catalyst.

The catalyst obtainable by the process of the invention preferably has a BET surface area in the range from 250 to 450 m$^2$/g, especially in the range from 270 to 410 m$^2$/g and more preferably in the range from 300 to 390 m$^2$/g, determined in accordance with DIN 66131. A sufficiently long synthesis period in the production of the zeolite powder maximizes the BET surface area, but it is lowered by the subsequent phosphorus modification with rising phosphorus content. The parameters (for example duration or temperature) of the calcination and of the steam treatment likewise have a crucial influence on the surface area.

Preferably, the pore volume of the catalyst of the invention, measured by the mercury porosimetry method in accordance with DIN 66133, is 0.3 to 0.8 cm$^3$/g, especially 0.30 to 0.45 cm$^3$/g.

The catalyst of the invention can be used particularly advantageously in processes for producing olefins by the conversion of oxygenates such as methanol or dimethyl ether.

In principle, however, use is also possible in other carbon conversion reactions, such as particularly dewaxing processes, alkylations, the conversion of paraffins to aromatic compounds (CPA) and related reactions.

Part of the invention, therefore, is a process for preparing olefins from oxygenates, preferably from methanol, dimethyl ether or mixtures thereof, wherein a reactant gas, i.e. the gaseous starting material, is passed over the catalyst of the invention. In the context of the present invention, oxygenates are understood to mean oxygen compounds, especially organic oxygen compounds such as alcohols and ethers. The present invention therefore preferably relates to a process for producing lower olefins, especially $C_2$ to $C_6$ olefins, from oxygen compounds (Oxygenates to Olefins, OTO), preferably from alcohols and/or ethers, more preferably from methanol (Conversion of Methanol to Olefins, CMO) or dimethyl ether by conversion, for example, of a reaction mixture comprising methanol vapor or dimethyl ether vapor and steam in a reactor over an indirectly cooled catalyst of the invention.

Directly upstream of the catalytic reaction, the catalyst of the invention can be subjected to a steam treatment. In a particularly preferred embodiment, the catalyst prepared in accordance with the invention is used directly in the catalytic reaction, i.e. without a prior steam treatment.

In the process of the invention, the methanol conversion in particular within a reaction cycle is increased, without lowering the propylene selectivity as in the case of other modification routes. By improving the hydrothermal stability, particularly in later reaction cycles (after an advanced total service life), the methanol conversion is reduced less significantly than in the case of the unmodified catalyst, such that the lifetime of the catalyst is additionally increased. Furthermore, the propylene yield and the propylene selectivity can be increased further by increasing the temperature, with lowering of the lifetime to a less significant degree than would be the case for the unmodified catalyst with the same temperature increase. Lifetime is understood to mean the duration of the catalyzed conversion to hydrocarbons by which the conversion drops to the same value (for example not less than 95%). It is thus possible to attain a maximum increase in the propylene yield without losses in the lifetime by increasing the temperature in the process for conversion of oxygenates such as methanol or dimethyl ether to olefins. In addition, the side crushing strength is also increased with respect to the underlying unmodified catalyst. The preparation process of the invention reduces the number of necessary process steps; there is no need for a repeated modification with a phosphorus compound in a later process step and a further treatment with acid to reduce the aluminum content after the steam treatment. Additionally provided is a process which allows the preparation of a catalyst which can be used directly by the process user without time-consuming and costly steam treatment prior to the catalytic conversion reaction.

It is found that the sequence of treatment of the zeolite-containing extrudate has a crucial influence on the product composition in the conversion of methanol to olefins and distinctly increases the lifetime of the catalyst.

Thus, the process of the invention, in which a steam treatment of the extrudate is first effected, followed by a phosphorus treatment, leads to an increase in the propylene yield, whereas, for example, a modification as known from DE 10 2011 013 909, in which a phosphorus modification is conducted first, followed by a subsequent steam treatment, leads to a decrease in the propylene yield (cf. test run 6, catalysts 7 to 10, and test run 8, comparative catalysts 13 to 16).

In addition, an increase in the lifetime of the catalyst of the invention with respect to the unmodified catalyst is observed. Thus, in test run 6, the lifetime of the catalyst, which is about 260 h for the unmodified reference catalyst 0, increases significantly with increasing phosphorus content and results especially in nearly twice as high a lifetime of about 516 h (see table 2, test run 6, catalysts 0 and 9). By contrast, a phosphorus modification as known from DE 10 2011 013 909 also leads to a measurable increase in the lifetime of the catalyst, but this increase is much smaller than for the catalyst of the invention and, moreover, cannot be influenced via the amount of phosphorus applied either (see table 2, test run 8, comparative catalysts 13 to 16).

In addition, it is observed that the amount of phosphorus applied affects the propylene yield. Thus, the propylene yield increases with increasing phosphorus content until it assumes a maximum value at a phosphorus content of about 1.4% by weight. A higher phosphorus content, by contrast, leads to a decrease in the propylene yield again.

In addition, there is an opposing trend which is expressed in the fact that the formation of aromatics is reduced with rising phosphorus content. The minimum value is attained for a phosphorus content of about 1.6% by weight. Since the formation of aromatics in a conversion of oxygenates to olefins is associated with the formation of carbonaceous deposits, a catalyst of the invention having a phosphorus content of about 1.6% by weight features an increase in the propylene yield, a prolonged lifetime and minimum formation of aromatics as by-products.

The reaction of methanol with the catalyst of the invention is preferably effected at a total pressure in the range from 0.1 to 1.5 bar, especially at a total pressure in the range from 0.5 to 1.4 bar, at a weight ratio of water and methanol or methanol equivalents in the range from 0.1 to 4.0, especially in the range from 0.5 to 3, and at a temperature of the reactor cooling medium in the range from 280° C. to 570° C., preferably in the range from 400° C. to 550° C. Such a process is described in EP 0 448 000 A1, the disclosure of which in this regard is hereby incorporated into the description. Further preferred processes are described in EP 1 289 912 A1 and DE 10 2006 026 103 A1, the disclosures of which are hereby incorporated into the description.

The present invention is elucidated by the nonlimiting examples which follow.

Preferred embodiments of the invention are described hereinafter.

1. A process for preparing a phosphorus-containing catalyst, comprising the following steps:
    (a) extruding a mixture comprising a zeolite and a binder,
    (b) calcining the extrudate obtained from step (a),
    (c) treating the calcined extrudate obtained from step (b) with steam,
    (d) applying a phosphorus compound to the steam-treated extrudate from step (c), and
    (e) calcining the phosphorus-modified extrudate from step (d),
    where the proportion by weight of phosphorus in the catalyst obtained after step (e) is 0.8% to 2.5% by weight, based on the total weight of the catalyst.
2. The process as claimed in embodiment 1, wherein the proportion by weight of phosphorus in the catalyst obtained after step (e) is 1.0% to 1.8% by weight, based on the total weight of the catalyst.
3. The process as claimed in embodiment 2, wherein the proportion by weight of phosphorus in the catalyst obtained after step (e) is about 1.4% by weight, based on the total weight of the catalyst.
4. The process as claimed in embodiment 1, 2 or 3, wherein the zeolite used in step (a) has a phosphorus content of 0% by weight to 0.01% by weight, preferably of 0% by weight to 0.001% by weight, and is especially a phosphorus-free zeolite.
5. The process as claimed in any of the preceding embodiments, wherein
    (i) both between the extrusion in step (a) and the calcination in step (b) and after the application of a phosphorus compound in step (c), there is no treatment with steam and
    (ii) both before the treatment of the extrudate with steam in step (c) and after the calcination of the phosphorus-modified extrudate in step (e), there is no application of a phosphorus compound.

6. The process as claimed in any of embodiments 1 to 5, wherein the mixture in step (a) comprises an acid selected from sulfuric acid, nitric acid, acetic acid, formic acid, oxalic acid and citric acid, preferably selected from nitric acid, acetic acid and citric acid, and more preferably citric acid and/or nitric acid.
7. The process as claimed in any of embodiments 1 to 6, wherein the treatment with steam in step (c) is conducted at a partial steam pressure in the range from 0.1 to 1 bar, a temperature in the range from 400° C. to 850° C., a WHSV in the range from 0.01 to 10 h$^{-1}$ and for 0.5 to 100 h, preferably at a partial steam pressure of about 1 bar, a temperature in the range from 400° C. to 650° C., a WHSV of about 1 h$^{-1}$ for about 48 h.
8. The process as claimed in any of embodiments 1 to 7, wherein the zeolite has a TON structure, MTT structure, MFI structure, MEL structure, MTW structure or EUO structure, and or mixtures thereof, preferably an MFI structure, more preferably a structure of the ZSM-5 type.
9. The process as claimed in any of embodiments 1 to 7, wherein the zeolite has an Si/Al atomic ratio in the range from 50 to 250, preferably in the range from 50 to 150, more preferably in the range from 75 to 140, most preferably in the range from 85 to 125.
10. The process as claimed in any of embodiments 1 to 9, wherein the zeolite consists of primary alumino silicate crystallites having a mean diameter in the range from 0.010 μm to 0.100 μm, more preferably in the range from 0.010 μm to 0.060 μm, and most preferably in the range from 0.015 μm to 0.050 μm.
11. The process as claimed in any of embodiments 1 to 10, wherein the zeolite is in the H form.
12. The process as claimed in any of embodiments 1 to 11, wherein the binder present in the mixture extruded in step (a) is aluminum oxide, magnesium oxide, titanium oxide, zinc oxide, niobium oxide, zirconium oxide, silicon oxide, hydrates thereof and/or a mixture thereof, preferably aluminum oxide or aluminum oxide hydrate, more preferably aluminum oxide hydrate.
13. The process as claimed in any of embodiments 1 to 12, wherein the binder present in the mixture extruded in step (a) is used in an amount in the range from 5% to 60% by weight, preferably in the range from 8% to 40% by weight, more preferably in the range from 10% to 35% by weight, based on the total weight of zeolite used and binder.
14. The process as claimed in any of embodiments 1 to 13, wherein the calcination in steps (b) and/or (e) is effected at a temperature in the range from 400° C. to 700° C., preferably at a temperature in the range from 500° C. to 600° C., for a duration of 1 h to 10 h, preferably for about 5 h, and more preferably at a temperature of about 550° C. for about 5 h.
15. The process as claimed in any of embodiments 1 to 14, wherein the phosphorus compound in step (d) is independently selected from inorganic phosphorus acids, organic phosphorus acids, alkali metal salts, alkaline earth metal salts and/or ammonium salts of inorganic phosphorus acids or organic phosphorus acids, phosphorus(V) halides, phosphorus(III) halides, phosphorus oxide halides, phosphorus(V) oxide, phosphorus(III) oxide and mixtures thereof.
16. The process as claimed in any of embodiments 1 to 14, wherein the phosphorus compound in step (d) is independently selected from $PY_5$, $PY_3$, $POY_3$, $M_xE_{z/2}H_{3-(x+z)}PO_4$, $M_xE_{z/2}H_{3-(x+z)}PO_3$, $P_2O_5$ and $P_4O_6$, in which Y is F, Cl, Br or I, preferably Cl,
x=0, 1, 2 or 3,
z=0, 1, 2 or 3,
where x+z≤3,
M is independently alkali metal and/or ammonium, and
E is alkaline earth metal.
17. The process as claimed in embodiment 16, wherein the phosphorus compound is selected from $H_3PO_4$, $(NH_4)H_2PO_4$, $(NH_4)_2HPO_4$ and $(NH_4)_3PO_4$, especially $H_3PO_4$ or $(NH_4)H_2PO_4$.
18. A catalyst obtainable by a process as claimed in any of embodiments 1 to 17.
19. The catalyst as claimed in embodiment 18, having a phosphorus content, based on the total weight of the catalyst, in the range from 0.8% to 2.5% by weight, preferably in the range from 1.0% to 1.8% by weight, and even more preferably of about 1.4% by weight.
20. A process for preparing olefins from oxygenates, wherein a reactant gas, preferably a gas comprising methanol, dimethyl ether and/or a mixture thereof, is passed over a catalyst as claimed in embodiment 18 or 19.
21. The use of a catalyst as claimed in embodiment 18 or 19 for converting oxygenates to olefins, especially for converting methanol to olefins.

EXAMPLES

Test Methods

The mean primary crystallite size was determined as described above with the aid of scanning electron analyses.
The scanning electron analyses were effected with a LEO Field Emission Scanning Electron Microscope (LEO Electron Microscopy Inc., USA) using powder samples of the catalyst which, beforehand, had been redispersed in acetone, treated with ultrasound for 30 seconds and then applied to a carrier (Probe Current Range: 4 pA to 10 nA). The measurement was effected at 80 000-fold magnification. It was possible to confirm the values at 253 000-fold magnification.

The mean side crushing strength was determined from the force that acts on the lateral face (longest side) of the shaped bodies before fracture occurs. For this purpose, from a representative sample of shaped bodies, 50 shaped bodies having a length in the range from 5.5 to 6.5 mm were selected and analyzed individually. The shaped bodies were free of cracks and straight. One shaped body was placed between two measurement jaws (one moving and one fixed). The moving measurement jaw was then moved uniformly onto the shaped body until fracture of the shaped body occurred. The fracture measurement value in kiloponds (kp), measured with a Schleuniger measuring instrument, was divided by the length of the shaped body in order to obtain the side crushing strength of the shaped body. 50 individual measurements were then used to determine the mean side crushing strength as the arithmetic mean.

The specific surface area (BET surface area) was determined in accordance with DIN 66131 using nitrogen.

The measurement of the pore volume by the mercury porosimetry method and the calculation of the pore diameter were effected in accordance with DIN 66133.

The mean methanol conversion was measured as described in use example 1 which follows.

Reference Example 1

Preparation of an H Zeolite Having a Mean Primary Crystallite Size of 0.03 μm

A reaction mixture was prepared by intimately mixing a suspension and a solution at room temperature in a 40 liter autoclave. The suspension was prepared by dissolving 2218 g of tetrapropylammonium bromide in 11 kg of deionized water and then introducing 5000 g of a commercial silica. The solution was prepared by dissolving 766 g of NaOH and then 45.6 g of NaAlO$_2$ in 5.5 liters of deionized water. The still-warm (25° C.-50° C.) solution was added to the suspension. The autoclave was then closed and brought to the reaction temperature while stirring at about 60 rpm. The reaction was ended after about 23 h, in order to stop the growth of the primary crystallites at a mean particle diameter of 0.03 µm. After cooling, the autoclave was opened, and the reaction mixture was removed from the reaction vessel and filtered. The filtercake was slurried in about 40 liters of deionized water, about 5 liters of a 0.4% by weight aqueous suspension of a commercial flocculant (Praestol BC 11L, copolymer of acrylamide and a cationic acrylic acid derivative) were added, and, after the stirring and settling of the pre-agglomerates of the solid material, the mixture was decanted. The wash process described was repeated until the wash water had a pH of 7 to 8 and a Br concentration of less than 1 ppm. The slurry, in which the pre-agglomerates of primary crystallites were apparent, held together by the flocculant, was filtered. The filtercake was then dried at 120° C. for 12 h.

The dried filtercake was comminuted to a grain size of 2 mm with a commercial granulator.

The granular material was brought to 350° C. at a heating rate of 1° C./minute under nitrogen (1000 L (STP)/h) and calcined at 350° C. under nitrogen (1000 L (STP)/h) for 15 h. Then the temperature was increased to 540° C. at a heating rate of 1° C./minute, and the granular material was calcined under air at this temperature for 24 h, in order to burn off the residual tetrapropylammonium bromide; finally, a calcined Na zeolite was obtained.

The calcined Na zeolite was suspended in 5 times the amount of a 1 molar aqueous HCl solution and brought to 80° C. The mixture was stirred at this temperature for one hour. Then about 1 liter of a 0.4% by weight suspension of the flocculant was added, and the supernatant acid, after the solids had settled out, was decanted. The operation thus described was repeated once more. In each of about 10 washing operations, the solids were suspended in 60 liters of deionized water while stirring and an average of 100 mL of a 0.4% by weight suspension of the flocculant was added. After the solids had settled out, the supernatant solution was decanted. Once the content of Cl$^-$ in the wash water was <5 ppm, the suspension was filtered off and the filtercake was dried at 120° C. for 15 h, in order to obtain a zeolite in the H form (ZSM-5 H zeolite).

The dried H zeolite was comminuted to 2 mm with a commercial granulator, brought to 540° C. at a heating rate of 1° C./minute under air and calcined at this temperature under air for 10 h.

The BET surface area of the zeolite thus obtained was 434 m$^2$/g.

The mean particle diameter of the primary crystallites was 0.03 µm. The Si/Al ratio was 105:1.

Reference Example 2: Preparation of Reference Catalyst 0

3400 g of the ZSM-5 H zeolite prepared in reference example 1 were mixed with 848 g of aluminum oxide hydrate and 136 g of paraffin wax. To this mixture were then added 1190 g of distilled H$_2$O, 233.7 g of a nitric acid solution (5% by weight of HNO$_3$) and 495 g of distilled H$_2$O. A plasticizable material is obtained. This was blended with 272 g of steatite oil.

The shaping (extrusion) was effected by means of a commercial extruder. The extruded shaped catalyst bodies had a diameter of about 3 mm and a length of about 6 mm. The extruded shaped catalyst bodies were dried at 120° C. and calcined at 550° C. for 5 h, and catalyst 0 is obtained. The BET surface area of the catalyst was determined to be 391 m$^2$/g. The side crushing strength was determined to be 0.66 kp/mm (6.47 N/mm), and the pore volume to be 0.33 mL/g.

Example 1

Preparation of Inventive Catalyst 1

32 g of catalyst 0 prepared in reference example 2 were heated to 480° C. at a heating rate of 1° C./min under a nitrogen flow of 400 mL/min. Thereafter, the catalyst, without a nitrogen flow, was treated with steam at 480° C. for 48 h, in the course of which 32 g of liquid water per hour were delivered constantly with an HPLC pump and evaporated at a partial pressure of 1 bar, heated to 480° C. and passed over the catalyst. This corresponds to a WHSV=1 g (water)/(g (catalyst)*h). Finally, the material was cooled to room temperature under a nitrogen flow.

To 25 g of the steam-treated catalyst in a 1 L round-bottom flask were added 250.42 g of a phosphoric acid solution (consisting of 249 g of water and 1.42 g of 85% by weight phosphoric acid (H$_3$PO$_4$), corresponding to about 0.48% by weight of H$_3$PO$_4$ in water), and the mixture was concentrated to dryness on a rotary evaporator at 85° C.-95° C. (initially 85° C., increased progressively up to 95° C.) at a pressure of 250 mbar over a period of about 3 h.

Thereafter, the product was dried at 120° C. for 5 h and calcined in air at 550° C. for 5 h. 25 g of the steam-treated and phosphorus-modified catalyst 1 are obtained.

The phosphorus content of the catalyst was 1.4% by weight. The BET surface area of the catalyst was determined to be 333 m$^2$/g. The side crushing strength was determined to be 0.96 kp/mm (6.43 N/mm), and the pore volume to be 0.31 mL/g.

Example 2

Preparation of Inventive Catalyst 6

Two batches each of 20 g of catalyst 0 prepared in reference example 2 were crushed with a mortar and pestle, and the sieve fraction of 200-280 µm was heated to 480° C. under a nitrogen flow. Thereafter, the catalyst, without a nitrogen flow, was treated with steam at 480° C. for 24 h, in the course of which, at a partial pressure of 1 bar, 1 g of liquid water per hour per gram of catalyst was delivered constantly, heated to 480° C. and passed over the catalyst. This corresponds to a WHSV=1 g (water)/(g (catalyst)*h). Finally, the material was cooled to room temperature under a nitrogen flow.

To 30 g of the steam-treated catalyst in a 1 L round-bottom flask were added 300.24 g of a phosphoric acid solution (consisting of 298 g of water and 2.24 g of 85% by weight phosphoric acid (H$_3$PO$_4$), corresponding to about 0.6% by weight of H$_3$PO$_4$ in water), and the mixture was concentrated to dryness on a rotary evaporator at 95° C. at a pressure of 250 mbar over a period of about 5 h.

Thereafter, the product was dried at 120° C. for 5 h and calcined in air at 550° C. for 5 h. 29 g of the steam-treated and phosphorus-modified catalyst 6 are obtained.

The phosphorus content of the catalyst was 1.8% by weight. The BET surface area of the catalyst was determined to be 340 m$^2$/g. The pore volume was determined to be 0.30 mL/g.

Comparative Example 1

Preparation of Comparative Catalyst 2

To 12 g of catalyst 1 prepared in example 1 were added 58.3 g of distilled H$_2$O, and the mixture was stirred at 90° C. for 1 h, filtered, washed, dried (15 h, 120° C.) and calcined (10 h, 540° C.), which afforded catalyst 2 having a phosphorus content of 1.5% by weight.

Comparative Example 2

Preparation of Comparative Catalyst 3

1400 g of the ZSM-5 H zeolite prepared in reference example 1 were suspended in 7066 g of phosphoric acid solution (about 0.8% by weight in water) at 80° C. to 90° C. for 2 h. Subsequently, the suspension was concentrated to dryness by means of a spray-drying process. This involved introducing the suspension through a nozzle at a temperature of about 220° C. into a NIRO spray drier. This affords a finely divided powder. The powder was then deposited in a cyclone. The powder was then calcined at 540° C. for about 10 h. The phosphorus content of the powder was 1.2% by weight. The BET surface area was determined to be 394 m$^2$/g.

850 g of the powder were slurried in 4130 mL of distilled H$_2$O and stirred at 90° C. for 1 h. Subsequently, the powder was filtered off, washed with 25 000 mL of water, dried at 120° C. for 18 h and then calcined at 540° C. for 10 h. A powder having a phosphorus content of 0.09% by weight is obtained. The BET surface area was determined to be 409 m$^2$/g.

700 g of the powder were mixed with 176 g of aluminum oxide hydrate and 28 g of paraffin wax. To this mixture were then added 245 g of distilled H$_2$O and 48.3 g of a nitric acid solution (5% by weight of HNO$_3$), followed by a further 120 g of distilled H$_2$O. A plasticizable material is obtained. This was blended with 56 g of steatite oil.

The shaping was effected by means of a commercial extruder. The extruded shaped catalyst bodies had a diameter of about 3 mm and a length of about 6 mm. The shaped catalyst bodies were dried at 120° C. for 18 h and calcined at 550° C. for 5 h, and catalyst 3 is obtained. The phosphorus content of the catalyst was 0.086% by weight. The BET surface area of the catalyst was determined to be 387 m$^2$/g. The side crushing strength was determined to be 0.90 kp/mm (8.85 N/mm), and the pore volume to be 0.34 mL/g.

Comparative Example 3

Preparation of Comparative Catalyst 4

1400 g of the ZSM-5 H zeolite prepared in reference example 1 were suspended in 7200 g of phosphoric acid solution (about 2.4% by weight in water) at 80° C. to 90° C. for 2 h. Subsequently, the suspension was concentrated to dryness by means of a spray-drying process. This involved introducing the suspension through a nozzle at a temperature of about 220° C. into a NIRO spray drier. This affords a finely divided powder. The powder was then deposited in a cyclone. The powder was then calcined at 540° C. for about 10 h. The phosphorus content of the powder was 3.4% by weight. The BET surface area was determined to be 296 m$^2$/g.

850 g of the powder were slurried in 4076 mL of distilled H$_2$O and stirred at 90° C. for 1 h. Subsequently, the powder was filtered off, washed with 26 000 mL of water, dried at 120° C. for 17 h and then in turn calcined at 540° C. for 10 h. The phosphorus content of the powder was 0.30% by weight. The BET surface area was determined to be 374 m$^2$/g.

700 g of the powder were mixed with 179 g of aluminum oxide hydrate and 28 g of paraffin wax. To this mixture were then added 245 g of distilled H$_2$O and 49.1 g of a nitric acid solution (5% by weight of HNO$_3$), followed by a further 115 g of distilled H$_2$O. A plasticizable material is obtained. This was blended with 56 g of steatite oil.

The shaping was effected by means of a commercial extruder. The extruded shaped catalyst bodies had a diameter of about 3 mm and a length of about 6 mm. The shaped catalyst bodies were dried at 120° C. for 16 h and calcined at 550° C. for 5 h, and catalyst 4 is obtained. The phosphorus content of the catalyst was 0.24% by weight. The BET surface area was determined to be 374 m$^2$/g. The side crushing strength was determined to be 0.91 kp/mm (8.91 N/mm), and the pore volume to be 0.33 mL/g.

Comparative Example 4

Preparation of Comparative Catalyst 5

1200 g of a ZSM-5 H zeolite prepared analogously to reference example 1, having a mean particle diameter of the primary crystallites of 0.03 μm, an Si/Al ratio of 99:1 and a BET surface area of 427 m$^2$/g, were suspended in 6050 g of a phosphoric acid solution (about 1.5% by weight in water) at 80° C. for 2 h. Subsequently, the suspension was concentrated to dryness by means of a spray-drying process. This involved introducing the suspension through a nozzle at a temperature of about 220° C. into a NIRO spray drier. This affords a finely divided powder. The powder was then deposited in a cyclone. The powder was then calcined at 540° C. for about 10 h. The phosphorus content of the powder was 2.3% by weight. The BET surface area was determined to be 327 m$^2$/g.

700 g of the powder were mixed with 179 g of aluminum oxide hydrate and 28 g of paraffin wax. To this mixture were then added 245 g of distilled H$_2$O and 48.0 g of a nitric acid solution (5% by weight of HNO$_3$), followed by a further 127 g of distilled H$_2$O. A plasticizable material is obtained. This was blended with 56 g of steatite oil.

The shaping was effected by means of a commercial extruder. The extruded shaped catalyst bodies had a diameter of about 3 mm and a length of about 6 mm. The shaped catalyst bodies were dried at 120° C. and calcined at 550° C. for 5 h, and catalyst 5 is obtained. The phosphorus content of the catalyst was 2.00% by weight. The BET surface area was determined to be 337 m$^2$/g. The pore volume was 0.43 cm$^3$/g. The measurement of the mean side crushing strength gave a value of about 0.14 kp/mm (1.37 N/mm).

Example 5

Preparation of Inventive Catalysts 7-10

The inventive catalysts 7-10 were prepared by first subjecting the reference catalyst 0 obtained from reference example 2 to a steam treatment according to example 2. 35 g of each steam-treated catalyst were phosphorus-modified with the aid of a rotary evaporator and analogously to the method described in example 1, by concentrating to dryness 175 g each time of a phosphoric acid solution including 1.32 g (catalyst 7), 1.85 g (catalyst 8), 2.39 g (catalyst 9) and 2.93 g (catalyst 10) of an 85% by weight phosphoric acid ($H_3PO_4$) (the difference from 175 g consisted of distilled $H_2O$). Thereafter, the product was dried at 120° C. for 4 h and calcined in air at 550° C. for 5 h. 35-36 g of the steam-treated and phosphorus-modified catalysts 7-10 are obtained. The phosphorus content of the catalysts was 0.95%, 1.22%, 1.63% and 2.10% by weight.

Comparative Example 6

Preparation of Comparative Catalysts 13-16

Comparative catalysts 13-16 were prepared as per the teaching of DE 10 2011 013 909.

For this purpose, the reference catalyst 0 which had not been subjected to prior steam treatment was laden with phosphorus by an incipient wetness method, by applying 19 g of a phosphoric acid solution to 50 g of reference catalyst 0 in each case. The 19 g of the phosphoric acid solution consisted here of an 85% by weight phosphoric acid ($H_3PO_4$) (1.9 g for preparation of comparative catalyst 13, 2.6 g for comparative catalyst 14, 3.4 g for comparative catalyst 15 and 4.2 g for comparative catalyst 16), and the difference from 19 g consisted of distilled $H_2O$. Thereafter, the respective product was dried at 120° C. for 4 h and calcined in air at 550° C. for 5 h. Subsequently, the catalysts were treated with steam.

TABLE 1

Chemical composition, specific surface area, pore volume and side crushing strengths of catalysts 0 to 10 and 13 to 16

| | P % by wt. | Si % by wt. | Al % by wt. | Specific surface area m²/g | Pore volume cm³/g | Side crushing strength kp/mm |
|---|---|---|---|---|---|---|
| Reference catalyst 0 | 0 | 37.6 | 8.4 | 391 | 0.33 | 0.66 |
| Catalyst 1 | 1.4 | 37.9 | 8.3 | 333 | 0.31 | 0.96 |
| Comparative catalyst 2 | 1.5 | 37.3 | 8.2 | 343 | 0.33 | — |
| Comparative catalyst 3 | 0.09 | 38.1 | 8.7 | 387 | 0.34 | 0.90 |
| Comparative catalyst 4 | 0.24 | 37.5 | 9.0 | 374 | 0.33 | 0.91 |
| Comparative catalyst 5 | 2.0 | 35.2 | 8.7 | 337 | 0.43 | 0.14 |
| Catalyst 6 | 1.8 | 36.9 | 8.2 | 340 | 0.30 | — |
| Catalyst 7 | 0.95 | 37.9 | 8.5 | 346 | 0.31 | — |
| Catalyst 8 | 1.22 | 37.8 | 8.4 | 344 | 0.31 | — |
| Catalyst 9 | 1.63 | 37.7 | 8.3 | 341 | 0.30 | — |
| Catalyst 10 | 2.10 | 37.0 | 8.2 | 337 | 0.29 | — |
| Comparative catalyst 13 | 1.0 | 39.1 | 8.6 | 374 | 0.31 | — |
| Comparative catalyst 14 | 1.4 | 38.8 | 8.5 | 362 | 0.30 | — |
| Comparative catalyst 15 | 1.8 | 38.1 | 8.3 | 357 | 0.30 | — |
| Comparative catalyst 16 | 2.3 | 38.4 | 8.3 | 361 | 0.29 | — |

Use Example 1: Comparison of Catalysts 0 to 4 and 6 in the Conversion of Methanol to Olefins The catalyst samples were examined for their catalytic characteristics in the conversion of methanol to olefins. This use example shows the advantages of the catalyst of the invention on the basis of catalytic data for the CMO process (Conversion of Methanol to Olefins process) in an isothermal fixed bed reactor.

300 mg of catalysts 0 to 4 and 6 were crushed with a mortar and pestle, the sieve fraction from 200 to 280 μm was diluted with silicon carbide (SiC) in a volume ratio of 1:4 (catalyst:SiC), and the mixture was introduced in each case into a vertical isothermal fixed bed reactor having an internal diameter of 8 mm.

Prior to the catalytic test, catalysts 0, 3 and 4 were heated to 480° C. under a nitrogen flow. Thereafter, the catalyst, without a nitrogen flow, was treated with steam at 480° C. (partial pressure 1 bar) for 24 h or 48 h (see table 2), by constantly delivering and evaporating 1 g of liquid water per 1 g of catalyst and hour at a partial pressure of 1 bar, heating it to 480° C. and guiding it over the catalyst. This corresponds to a WHSV=1 g (water)/(g (catalyst)*h). Finally, the catalyst was cooled to room temperature under a nitrogen flow. The lifetime of the standard depends significantly on the impurities in the feed. Therefore, the absolute lifetimes are comparable only for those catalysts that were tested in the same test run, i.e. using the same feed (table 2). To provide controls for the results, each catalyst is analyzed in at least two of the total of ten reactors in the same test run, a faultless test run having been identified in all cases on the basis of agreement of results (lifetime and selectivities).

The composition of the products at the outlet of the CMO catalyst reactor was determined by gas chromatography analysis methods.

The selectivity $S_i$ results from the molar carbon content of component i based on the carbon converted, calculated as the sum total over all the carbonaceous products obtained. The methanol (MeOH) and dimethyl ether (DME) reactants, the latter being in equilibrium with the former, are not included here among the products:

$$S_i = 100\% \cdot \frac{\dot{n}_{iout} \cdot \varepsilon_i^C}{\sum\limits_{i}^{i=8} \dot{n}_{iout} \cdot \varepsilon_i^C}$$

The yield $Y_i$ of a product results from the molar carbon content of component i based on the total carbon used. The total carbon used is calculated as the sum total over all carbonaceous products, plus the methanol (MeOH) and dimethyl ether (DME) reactants used, the latter being in equilibrium with the former:

$$Y_i = 100\% \cdot \frac{\dot{n}_{iout} \cdot \varepsilon_i^C}{\dot{n}_{MeOHout} \cdot \varepsilon_{MeOH}^C + \dot{n}_{DMEout} \cdot \varepsilon_{DME}^C + \sum\limits_{i}^{i=N} \dot{n}_{iout} \cdot \varepsilon_i^C}$$

The conversion $X_i$ results from the sum total over all the carbonaceous products obtained based on the total carbon used. The total carbon used is calculated as the sum total over all the carbonaceous products, plus the methanol (MeOH) and dimethyl ether (DME) reactants used, the latter being in equilibrium with the former:

$$X_i = 100\% \cdot \frac{\sum_{i}^{i=N} \dot{n}_{iout} \cdot \varepsilon_i^C}{\dot{n}_{MeOHout} \cdot \varepsilon_{MeOH}^C + \dot{n}_{DMEout} \cdot \varepsilon_{DME}^C + \sum_{i}^{i=N} \dot{n}_{iout} \cdot \varepsilon_i^C} = \sum_{i}^{i=N} Y_i$$

$S_i$: selectivity for component i
$X_i$: conversion of methanol and dimethyl ether
$Y_i$: yield of component i
$\varepsilon_i^c$: number of carbon atoms of component i
$\dot{n}_i$: molar flow rate of component i Inventive catalysts 1 and 6 and comparative catalyst 2 were not subjected to any further steam treatment in the reactor.

The methanol/water feed (parts by weight (MeOH:H$_2$O) =1:2) was guided over the catalyst in the reactor at a space velocity WHSV (methanol)=1.5 g (methanol)/(g (catalyst) *h), i.e. 4.5 g of total feed per g of catalyst and hour at a pressure of 1 bar, for conversion of methanol. 10 reactors are operated in parallel and each is supplied with the methanol-water mixture by means of a dedicated HPLC pump. The HPLC pumps each feed the feed via capillaries into an empty pre-reactor in which the feed is evaporated at 260° C. and fed to the reactor via a capillary. Each catalyst is analyzed simultaneously in at least two reactors in the same test run, in order to be able to identify a faultless test run on the basis of identical results. All products are separated and determined quantitatively by means of a gas chromatograph.

The lifetime is the duration of the catalytic reaction relative to reference catalyst 0 at a reaction temperature of 400° C. up to which the conversion is 95% or higher.

The propylene yield, ethylene yield and aromatics yield was determined as the mean at a methanol conversion of not less than 99.0% from the data of the product analysis by gas chromatography.

The methanol content at the reactor outlet was determined by gas chromatography analysis methods.

Use Example 2: Comparison of Catalysts 0, 7 to 10 and 13 to 16 in the Conversion of Methanol to Olefins Reference catalyst 0, inventive catalysts 7 to 10 and comparative catalysts 13 to 16 were tested in accordance with the method described in use example 1 as catalysts in the conversion of methanol to olefins.

In this case, the inventive catalysts were not subjected to any further steam treatment; reference catalyst 0 and comparative catalysts were subjected to a steam treatment as described in use example 1, with a duration of 24 h.

The reaction temperature was 475° C.; the propylene yields, ethylene yields and aromatics yields in the case of use of the catalysts and the lifetime thereof are summarized in table 2.

TABLE 2

Results of the catalytic tests on catalysts 0 to 4, 6 to 10 and 13 to 16

| Test run | Catalyst | Steam treatment [h] | Reaction temperature [° C.] | Propylene yield [%] | Ethylene yield [%] | Aromatics yield [%] | Lifetime [h] |
|---|---|---|---|---|---|---|---|
| 1 | 0 | 48 | 450° C. | ≈44.2 | ≈4.4 | ≈2.1 | ≈450 |
| 1 | 0 | 48 | 475° C. | ≈47.8 | ≈5.3 | ≈1.9 | ≈280 |
| 1 | 1 | 48 | 450° C. | ≈44.6 | ≈4.4 | ≈1.9 | ≈675 |
| 1 | 1 | 48 | 475° C. | ≈49.2 | ≈5.3 | ≈1.6 | ≈550 |
| 2 | 0 | 24 | 450° C. | ≈43.0 | ≈4.7 | ≈1.7 | ≈250 |
| 2 | 0 | 24 | 475° C. | ≈46.3 | ≈6.1 | ≈1.7 | ≈203 |
| 2 | 1 | 48 | 475° C. | ≈47.7 | ≈6.1 | ≈1.6 | ≈322 |
| 2 | 6 | 24 | 475° C. | ≈48.0 | ≈5.6 | ≈1.3 | ≈296 |
| 3 | 0 | 48 | 450° C. | ≈42.3 | ≈4.4 | ≈2.4 | ≈350 |
| 3 | 2 | 48 | 450° C. | ≈43.9 | ≈3.9 | ≈2.3 | ≈235 |
| 4 | 0 | 24 | 450° C. | ≈43 | ≈4 | ≈2 | ≈95 |
| 4 | 3 | 24 | 450° C. | ≈37 | ≈6 | ≈3 | ≈117 |
| 4 | 4 | 24 | 450° C. | ≈33 | ≈8 | ≈4 | ≈133 |
| 5 | 0 | 24 | 450° C. | ≈41.3 | ≈4.2 | ≈2.8 | ≈180 |
| 5 | 6 | 24 | 450° C. | ≈43.1 | ≈4.0 | ≈2.2 | ≈330 |
| 6 | 0 | 24 | 475° C. | ≈47.1 | ≈5.0 | ≈1.5 | ≈260 |
| 6 | 7 | 24 | 475° C. | ≈47.4 | ≈5.1 | ≈1.3 | ≈377 |
| 6 | 8 | 24 | 475° C. | ≈47.8 | ≈5.2 | ≈1.3 | ≈444 |
| 6 | 9 | 24 | 475° C. | ≈48.5 | ≈5.2 | ≈1.1 | ≈545 |
| 6 | 10 | 24 | 475° C. | ≈48.4 | ≈5.1 | ≈1.2 | ≈515 |
| 7 | 0 | 24 | 475° C. | ≈47.5 | — | — | ≈180 |
| 7 | 6 | 24 | 475° C. | ≈48.1 | — | — | ≈440 |
| 8 | 0 | 24 | 475° C. | ≈46.9 | — | — | ≈190 |
| 8 | 13 | 24 | 475° C. | ≈45.4 | — | — | ≈295 |
| 8 | 14 | 24 | 475° C. | ≈44.8 | — | — | ≈305 |
| 8 | 15 | 24 | 475° C. | ≈44.6 | — | — | ≈290 |
| 8 | 16 | 24 | 475° C. | ≈44.4 | — | — | ≈285 |

Table 2 collates the propylene yield, ethylene yield and aromatics yield in the case of use of catalysts 0, 1, 2, 3, 4 and 6 and the lifetime thereof at a reaction temperature of 450° C. (temperature of the reactor), and the propylene yield, ethylene yield and aromatics yield in the case of use of catalysts 0 and 1 and the lifetime thereof at a reaction temperature of 475° C. (temperature of the reactor).

The duration of the steam treatment in table 2 relates to the steam treatment during the synthesis for catalysts 1, 2 and 6 to 10, and to the steam treatment prior to the reaction for catalysts 0, 3 and 4 (this final steam treatment is dispensed with for catalysts 1, 2 and 6 to 10).

As apparent from table 2, it is a feature of inventive catalysts 1 and 6 to 10 that the lifetime of the catalyst is increased without causing any measurable adverse effect on the propylene yield.

Figure 6:
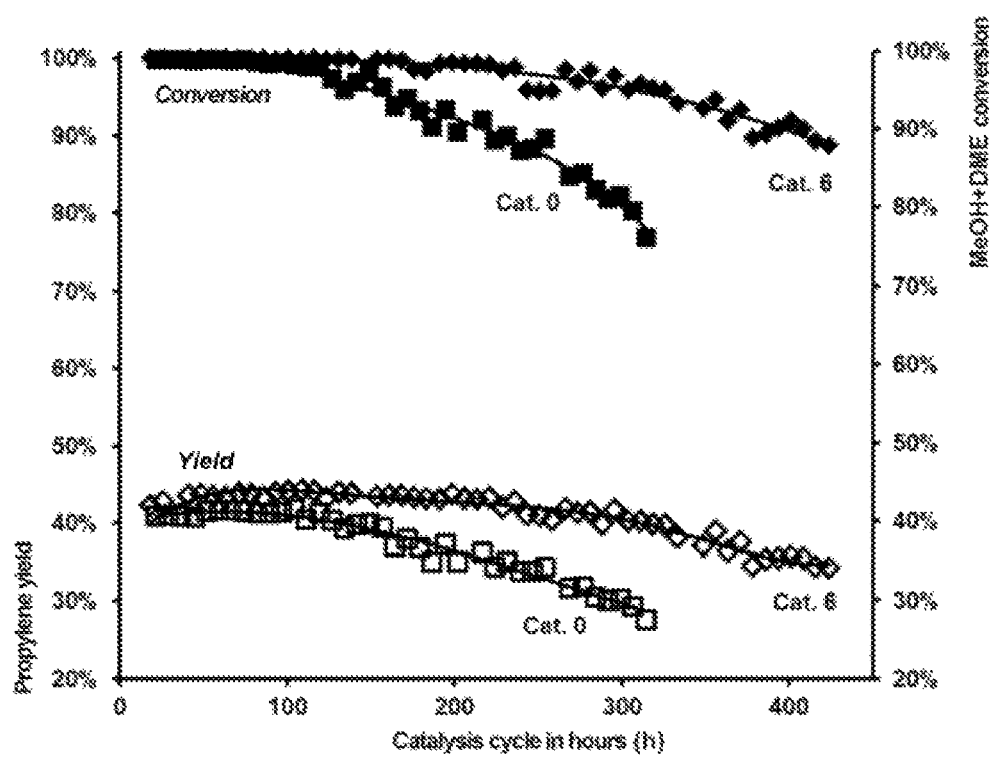
FIG. 6 shows the conversion of methanol to propylene over reference catalyst 0 at 450° C. and over inventive catalyst 6 at 450° C. in each case. Cat. 0: methanol conversion ■, propylene yield □; Cat. 6: methanol conversion ♦, propylene yield ◊. Steam treatment for 24 h in each case.
Figure 7:
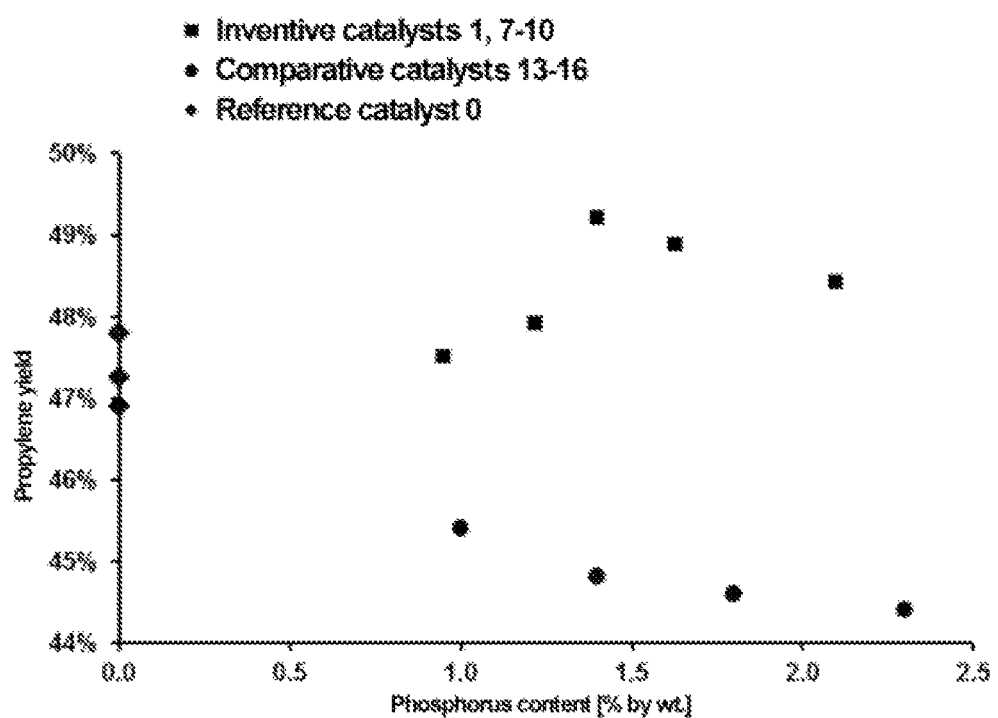
FIG. 7 shows the dependence of the propylene yield on the phosphorus content of the catalyst for inventive catalysts 1 and 7 to 10 and for comparative catalysts 13 to 16.

The advantage of inventive catalyst 1 becomes clear particularly in the comparison of the conversion at 475° C. with the conversion over reference catalyst 0 at 450° C.: the propylene yield is increased by about 5% (absolute), whereas the lifetime of inventive catalyst is still increased by 35% compared to reference catalyst 0 at 450° C. (see also FIG. 1). For catalyst 6 too, it is found that the propylene selectivity can be increased by increasing the temperature without reducing the lifetime (see also FIG. 6).

Figure 2:
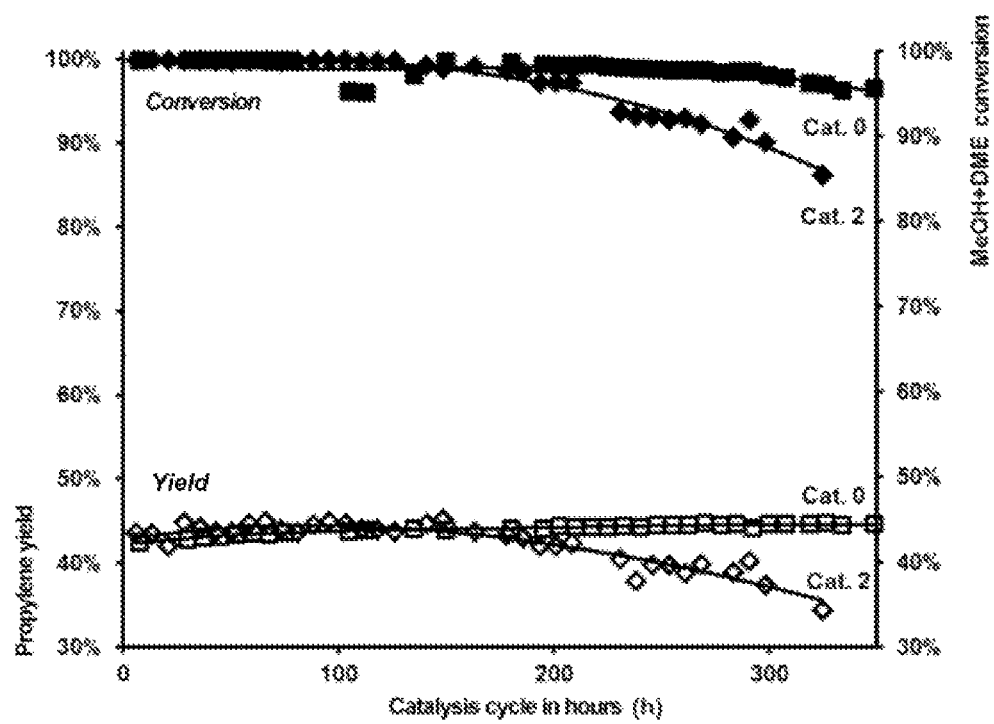
FIG. 2 shows the conversion of methanol to propylene over reference catalyst 0 at 450° C. and over comparative catalyst 2 at 450° C. in each case. Cat. 0: methanol conversion ■, propylene yield □; Cat. 2: methanol conversion ♦, propylene yield ◊. Steam treatment for 48 h in each case.
Figure 3:
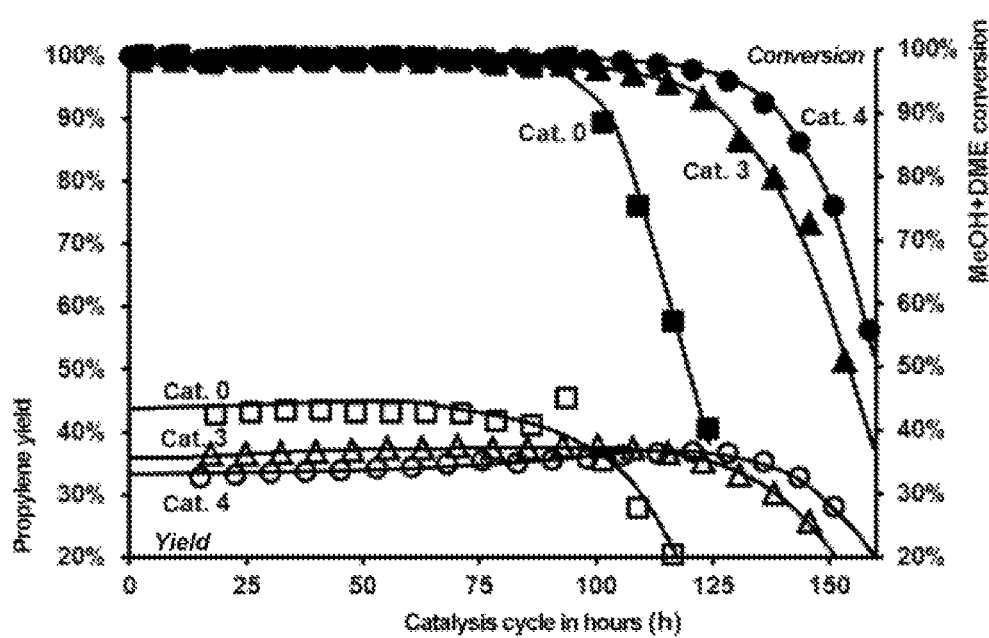
FIG. 3 shows the conversion of methanol to propylene over reference catalysts 3 and 4 at 450° C. and over reference catalyst 0 at 450° C. in each case. Cat. 3: methanol conversion ▲, propylene yield ∆; Cat. 4: methanol conversion ●, propylene yield ○; Cat. 0: methanol conversion ■, propylene yield □. Steam treatment for 24 h in each case.

As can be inferred from table 2, by contrast, the comparative catalysts feature either a shorter lifetime (comparative catalyst 2, see also FIG. 2) or a lower propylene yield (comparative catalyst 3 and comparative catalyst 4, see also FIG. 3) compared to reference catalyst 0.

Figure 4:
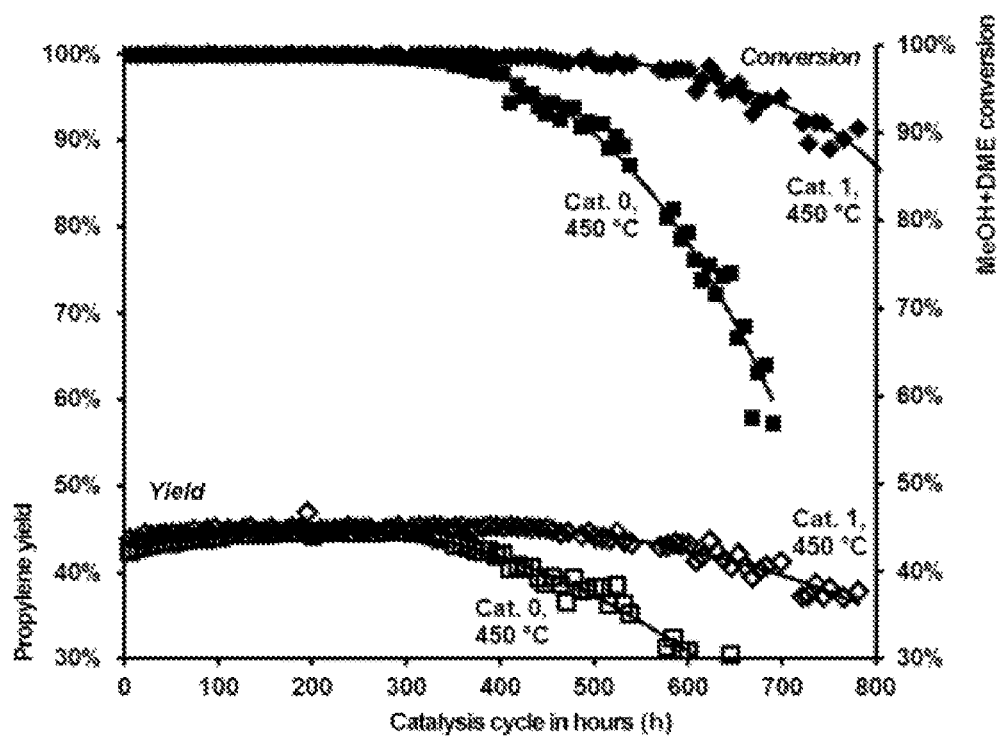
FIG. 4 shows the conversion of methanol to propylene over reference catalyst 0 at 450° C. and over inventive catalyst 1 at 450° C. in each case. Cat. 0: methanol conversion ■, propylene yield □; Cat. 1: methanol conversion ♦, propylene yield ◊. Steam treatment for 48 h in each case.
Figure 5:
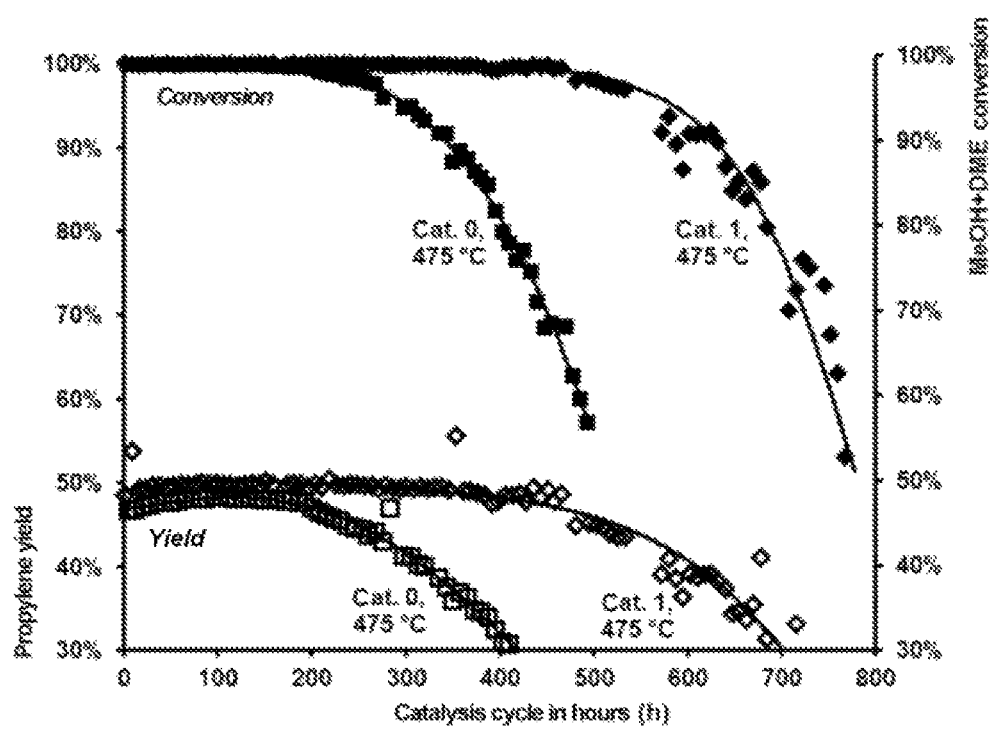
FIG. 5 shows the conversion of methanol to propylene over reference catalyst 0 at 475° C. and over inventive catalyst 1 at 475° C. in each case. Cat. 0: methanol conversion ■, propylene yield □; Cat. 1: methanol conversion ♦, propylene yield ◊. Steam treatment for 48 h in each case.

Especially at higher reaction temperatures, the lifetime of the catalysts is shortened: if the reaction is conducted at 475° C. rather than at 450° C., the lifetime of reference catalyst 0 is reduced to about 70% (compared to reference catalyst 0 at 450° C.). For inventive catalyst 1, the lifetime is reduced only to about 90% (compared to catalyst 1 at 450° C.) when the conversion is conducted at 475° C. rather than at 450° C. By virtue of the elevated stability to carbonization, inventive catalyst 1 has nearly twice as long a lifetime compared to reference catalyst 0 at 475° C. (see FIGS. 4 and 5).

The washing of the phosphorus-containing zeolite powder in the synthesis of comparative catalysts 3 and 4 reduces its original phosphorus content (comparative catalyst 3: 1.2% by weight of P prior to washing; comparative catalyst 4: 3.4% by weight of P prior to washing). In spite of the low phosphorus content, comparative catalysts 3 and 4 have an increased lifetime. However, the propylene yield and propylene selectivity is reduced. By contrast, a wash step after the extrusion, which does not lead to reduction in the initial phosphorus content and does not have any significant effect on propylene selectivity and propylene yield (comparative catalyst 2), results in a reduction in the lifetime.

If the propylene selectivity of comparative catalysts 3 and 4 in the conversion of methanol to propylene is compared, it is clear that an increase in the phosphorus content in the phosphorus modification of zeolite powder (cf. comparative catalyst 3: 1.2% by weight of P; increased in the case of comparative catalyst 4: 3.4% by weight of P) with subsequent washing prior to extrusion leads to a deterioration in the propylene selectivity. In order to prepare a catalyst having a phosphorus content comparable to inventive catalyst 1 by this synthesis route, the initial phosphorus content would have to be increased well above that of catalyst 4. It can be inferred from this that an even more significant reduction in propylene selectivity would be expected in the case of a catalyst prepared by this route. Thus, a catalyst of this kind would be all the less suitable for the conversion of oxygenates to olefins.

A catalyst comparable to inventive catalyst 1 and having a similarly high phosphorus content (comparative catalyst 5) of about 2.0% by weight, which is prepared by phosphorus modification of the zeolite powder without washing, is only of inadequate suitability for further processing to a shaped body, since the mechanical stability thereof (side crushing strength about 0.14 kp/mm (1.37 N/mm)) is so low that problems arise here in the transport and filling of the reactor, since the shaped bodies break up very rapidly.

Furthermore, it is found that the sequence of treatment of the zeolite-containing extrudate has a crucial influence on the product composition in the conversion of methanol to olefins and distinctly increases the lifetime of the catalyst.

Thus, the process of the invention in which an initial steam treatment of the extrudate is followed by a phosphorus treatment leads to an increase in the propylene yield, whereas, for example, a modification as known from DE 10 2011 013 909, in which an initial phosphorus modification is followed by a subsequent steam treatment, leads to a decrease in the propylene yield (cf. test run 6, catalysts 7 to 10, and test run 8, comparative catalysts 13 to 16).

Moreover, an increase in the lifetime of the catalyst of the invention compared to the unmodified catalyst is observed. Thus, in test run 6, the lifetime of the catalyst, which is about 260 h for the unmodified reference catalyst 0, increases significantly with increasing phosphorus content and results, more particularly, in nearly twice as high a lifetime of about 516 h (see table 2, test run 6, catalysts 0 and 9). By contrast, a phosphorus modification as known from DE 10 2011 013 909 also leads to a measurable increase in the lifetime of the catalyst, but this increase is much smaller than for the inventive catalyst and, moreover, also cannot be influenced via the amount of phosphorus applied (see table 2, test run 8, comparative catalysts 13 to 16).

Furthermore, it is observed that the amount of phosphorus applied affects the propylene yield. Thus, the propylene yield increases with increasing phosphorus content until it assumes a maximum value at a phosphorus content of about 1.4% by weight. A higher phosphorus content, by contrast, leads to a decrease in the propylene yield again.

The invention claimed is:

1. A process for preparing a phosphorus-containing catalyst, comprising the steps of:
    (a) extruding a mixture comprising a zeolite having an MFI structure, having an Si/Al atomic ratio in the range from 85 to 125, and aluminum oxide, aluminum oxide hydrate or both as a binder to obtain an extrudate,
    (b) calcining the extrudate obtained from step (a),
    (c) treating the calcined extrudate obtained from step (b) with steam,
    (d) applying a phosphorus compound to the steam-treated extrudate from step (c) to obtain a phosphorus-containing extrudate, and
    (e) calcining the phosphorus-modified extrudate from step (d) thereby producing a phosphorus-containing catalyst,
wherein the proportion by weight of phosphorus in the catalyst obtained after step (e) is 0.8% to 2.5% by weight, and wherein the binder present in the mixture extruded in step (a) is used in an amount in the range from 8% to 40% by weight, based on the total weight of zeolite used and binder, and
wherein
    (i) both between the extrusion in step (a) and the calcination in step (b) and after the application of a phosphorus compound in step (d), there is no treatment with steam, and
    (ii) both before the treatment of the extrudate with steam in step (c) and after the calcination of the phosphorus-modified extrudate in step (e), there is no application of a phosphorus compound.

2. The process as claimed in claim 1, wherein the proportion by weight of phosphorus in the phosphorus-containing catalyst obtained after step (e) is 1.0% to 1.8% by weight, based on the total weight of the phosphorus-containing catalyst.

3. The process as claimed in claim 1, wherein the proportion by weight of phosphorus in the phosphorus-containing catalyst obtained after step (e) is about 1.4% by weight based on the total weight of the phosphorus-containing catalyst.

4. The process as claimed in claim 1, wherein the zeolite used in step (a) has a phosphorus content of 0% by weight to 0.01% by weight.

5. The process as claimed in claim 1, wherein the zeolite consists of primary alumino-silicate crystallites having a mean diameter in the range from 0.010 μm to 0.100 μm.

6. The process as claimed in claim 1, wherein the calcination in steps (b), (e) or both, is effected at a temperature in the range from 400° C. to 700° C.

7. The process as claimed in claim 1, wherein the phosphorus compound in step (d) is independently selected from the group consisting of inorganic phosphorus acids, organic phosphorus acids, alkali metal salts, alkaline earth metal salts, ammonium salts of inorganic phosphorus acids or organic phosphorous acids, phosphorus(V) halides, phosphorus(III) halides, phosphorus oxide halides, phosphorous (V) oxide, phosphorus(III) oxide and mixtures thereof.

8. The process as claimed in claim 1, wherein the phosphorus compound in step (d) is independently selected from the group consisting of $PY_5$, $PY_3$, $POY_3$, $M_xE_{z/2}H_{3-(x+z)}PO_4$, $MxE_{z/2}H_{3-(x+z)}PO_3$, $P_2O_5$ and $P_4O_6$, in which Y is F, Cl, Br or I,
x=0, 1, 2 or 3,
z=0, 1, 2 or 3,
where x+z≤3,
M is independently alkali metal, ammonium or a mixture thereof, and
E is an alkaline earth metal.

9. The process as claimed in claim 1, wherein the zeolite used in step (a) has a phosphorus content of 0% by weight to 0.001% by weight.

10. The phosphorus as claimed in claim 1, wherein the zeolite used in step (a) is a phosphorus-free zeolite.

11. The process as claimed in claim 1, wherein the zeolite has a structure of the ZSM-5 type.

12. The process as claimed in claim 1, wherein the zeolite consists of primary alumino-silicate crystallites having a mean diameter in the range from 0.010 μm to 0.060 μm.

13. The process as claimed in claim 1, wherein the zeolite consists of primary alumino-silicate crystallites having a mean diameter in the range from 0.015 μm to 0.050 μm.

14. The process as claimed in claim 1, wherein the binder present in the mixture extruded in step (a) is aluminum oxide.

15. The process as claimed in claim 1, wherein the binder present in the mixture extruded in step (a) is aluminum oxide hydrate.

16. The process as claimed in claim 1, wherein the binder present in the mixture extruded in step (a) is used in an amount in the range from 10% to 35% by weight, based on the total weight of zeolite used and binder.

17. The process as claimed in claim 1, wherein the calcination in steps (b), (e) or both, is effected at a temperature in the range from 500° C. to 600° C. for a duration of 1 h to 10 h.

18. The process as claimed in claim 1, wherein the calcination in steps (b), (e) or both, is effected at a temperature in the range from 400° C. to 700° C. for about 5 h.

19. The process as claimed in claim 1, wherein the calcination in steps (b), (e) or both, is effected at a temperature in the range from 500° C. to 600° C. for about 5 h.

20. The process as claimed in claim 1, wherein the calcination in steps (b), (e) or both, is effected at a temperature of about 550° C. for about 5 h.

21. The process as claimed in claim 1, wherein the phosphorus compound in step (d) is independently selected from the group consisting of $H_3PO_4$, $(NH_4)H_2PO_4$, $(NH_4)_2HPO_4$ and $(NH_4)_3PO_4$.

22. The process as claimed in claim 1, wherein the phosphorus compound in step (d) is independently selected from the group consisting of $H_3PO_4$ and $(NH_4)H_2PO_4$.

* * * * *